United States Patent [19] [11] Patent Number: 5,013,852
Walenta et al. [45] Date of Patent: May 7, 1991

[54] 3-FLAVONE CARBOXYLIC ACID COMPOUNDS

[75] Inventors: Rainer Walenta, Wedemark; Reiner Müller-Peddinghaus, Bergisch-Gladbach; Ivan Ban, Hanover; Michael Wurl, Garbsen; Ulf Preuschoff, Laatzen, all of Fed. Rep. of Germany

[73] Assignee: Kali-Chemie Pharma GmbH, Hanover, Fed. Rep. of Germany

[21] Appl. No.: 353,606

[22] Filed: May 18, 1989

Related U.S. Application Data

[62] Division of Ser. No. 180,401, May 5, 1988, Pat. No. 4,886,806.

Foreign Application Priority Data

May 12, 1987 [DE] Fed. Rep. of Germany ....... 3715779

[51] Int. Cl.[5] ........................................... C07D 311/30
[52] U.S. Cl. ................... 549/362; 549/385; 549/402
[58] Field of Search ...................... 549/402, 385, 382

[56] References Cited

PUBLICATIONS

Ziegler et al., C.A., 55, 27297a–i (1961) (Monatsh. 92, 296–302 (1961)).
Costa et al., *J. Chem. Soc. Perkin I*, (1985) 799.
Hormi et al., C.A., 107, 217, 294m (1987), J. Org. Chem., 52, 5272–4 (1987).

*Primary Examiner*—Nicky Chan
*Attorney, Agent, or Firm*—Foley & Lardner

[57] ABSTRACT

Flavone-3-carboxylic acid compounds corresponding to the Formula I:

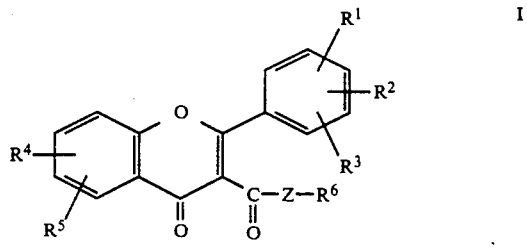

wherein $R^1$, $R^2$, $R^3$, $R^4$ and $R^5$ represent hydrogen, lower alkyl, halogen, hydroxy, or etherified or esterified hydroxy, and $Z-R^6$ stands for a basically substituted alkoxy or amino group, as well as processes and intermediate products for their production. The compounds exhibit inflammation-inhibiting pharmacological activity.

1 Claim, No Drawings

3-FLAVONE CARBOXYLIC ACID COMPOUNDS

This application is a division of application Ser. No. 07/190,401, filed May 5, 1988, now U.S. Pat. No. 4,886,806.

BACKGROUND OF THE INVENTION

The present invention relates to new basic flavone-3-carboxylic acid amide and ester compounds and their salts and N-oxides and to pharmaceutical preparations containing these compounds, processes for preparing them and intermediate flavone-3-carboxylic acid products.

In an article by A. Costa et al (J. Chem. Soc. Perkin I (1985), 799) on lithiation of flavones and reactions of the lithiated products, 3-flavone-carboxylic acid, 2'-methoxy-3-flavone-carboxylic acid and 5,7-dimethyl-3-flavone-carboxylic acid are described. Until now however, no pharmacological activity has been known for these compounds.

SUMMARY OF THE INVENTION

The object of the present invention is to develop new pharmaceuticals with inflammation-retarding properties.

It is another object of the present invention to prepare new flavone compounds with valuable pharmacological properties.

These and other objects are achieved according to the present invention by providing a flavone-3-carboxylic acid compound corresponding to the formula

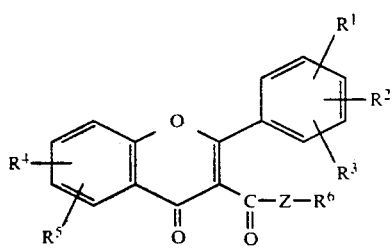

wherein
- $R^1$ represents hydrogen, lower alkyl, halogen, hydroxy, lower alkylcarbonyloxy or an $R^9$—O group, wherein $R_9$ represents an alkyl or alkenyl group with up to 20 carbon atoms,
- $R^2$ represents hydrogen, lower alkyl, halogen, hydroxy, lower alkylcarbonyloxy or an $R^9$—O group, wherein $R^9$ has the above meaning, and
- $R^3$ represents hydrogen, lower alkyl, halogen, hydroxy, lower alkylcarbonyloxy or an $R^9$—O group, wherein $R^9$ has the above meaning, or
- two of the substituent groups $R^1$ to $R^3$ are bonded to adjacent carbon atoms and together represent an alkylenedioxy group with 1 or 2 carbon atoms, with the proviso that if more than one of the substituent groups $R^1$ to $R^3$ represent oxygen-containing groups, these groups are identical,
- R4 represents hydrogen, lower alkyl, halogen, hydroxy, lower alkylcarbonyloxy or an $R^9$—O group, wherein $R^9$ has the above meaning, and
- $R^5$ represents hydrogen, lower alkyl, halogen, hydroxy, lower alkylcarbonyloxy or an $R^9$—O group, wherein $R^9$ has the above meaning, or
- $R^4$ and $R^5$ are bonded to adjacent carbon atoms and together form an alkylenedioxy group with 1 or 2 carbon atoms,
  with the proviso that if both $R^4$ and $R^5$ represent oxygen-containing groups, these groups are identical, and, if $R^1$, $R^2$ or $R^3$ represent hydroxy or lower alkylcarbonyloxy groups, oxygen-containing groups $R^4$ and $R^5$ are identical to these groups,
- $R^6$ represents a di(lower alkyl)amino group, a pyridyl group, a pyrimidyl group, a 1-benzylpiperidin-4-yl group, or a group corresponding to the formula

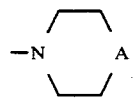  a wherein
- A represents a bond, a methylene group, oxygen or an N—$R^7$ group, wherein $R^7$ represents hydrogen, lower alkyl, pyridyl, pyrimidyl, benzyl, benzyl substituted by lower alkyl or halogen, phenyl or phenyl substituted by lower alkyl or halogen,
- Z represents a Y—$(CH_2)_n$- group, wherein
- Y represents an $NR^8$ group wherein $R^8$ is hydrogen or lower alkyl, or, if $R^1$ through $R^5$ are other than lower alkylcarbonyloxy or hydroxy, Y may also be oxygen, and
- n represents an integer from 2 to 4 or, if R6 is a 1-benzylpiperidin-4-yl group, n may also be zero, or p1 Z may also represent a bond if $R^6$ represents a group a in which A is an N—R⁻ group;

or an N-oxide or acid addition salt thereof.

According to further preferred aspects of the invention, the objects are also achieved by providing a process for preparing the forgoing flavone-3-carboxylic acid compounds and intermediate 3-flavone carboxylic acids useful in producing the forgoing flavone-3-carboxylic acid compounds.

DETAILED DESCRIPTION OF PREFERRED EMBODIMENTS

It has been found that new basic 3-flavone-carboxylic acid derivatives according to the invention have valuable pharmacological properties, in particular proeprties inhibiting the formation of oxygen radicals in inflammation cells, and also lipoxygenase-inhibiting properties and antiphlogistic properties and have a favorable activity profile with low toxicity and good compatibility. Because of their oxygen radical-sequestering properties, the substances have the effect of inhibiting inflammation and are suitable as anti-inflammatory drugs and antiphlogistic drugs for treating inflammatory and allergic conditions.

The present invention therefore relates to new basic flavone-3-carboxylic acid compounds of general Formula I

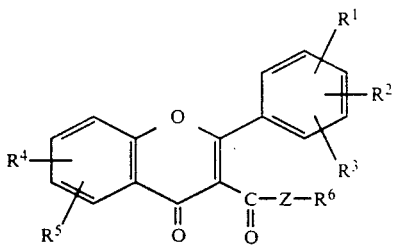

I wherein
- $R^1$ represents hydrogen, lower alkyl, halogen, hydroxy, lower alkylcarbonyloxy or an $R^9$—O group, wherein $R^9$ stands for an alkyl or alkenyl group with up to 20 carbon atoms,
- $R^2$ represents hydrogen, lower alkyl, halogen, hydroxy, lower alkylcarbonyloxy or an $R^9$—O group, wherein $R^9$ has the above meaning, and
- $R^3$ represents hydrogen, lower alkyl, halogen, hydroxy, lower alkylcarbonyloxy or an $R^9$—O group, wherein $R^9$ has the above meaning, or two of the substituents $R^1$ to $R^3$ are bonded to adjacent carbon atoms and together represent an alkylenedioxy group with 1 or 2 carbon atoms,
with the proviso that if several of the substituted groups $R^1$ to $R^3$ represent oxygen-containing radicals, these radicals are identical,
- $R^4$ represents hydrogen, lower alkyl, halogen, hydroxy, lower alkylcarbonyloxy or an $R^9$—O group, wherein $R^9$ has the above meaning, and
- $R^5$ represents hydrogen, lower alkyl, halogen, hydroxy, lower alkylcarbonyloxy or an $R^9$—O group, wherein $R^9$ has the above meaning, or
- $R^4$ and $R^5$ are bonded to adjacent carbon atoms and together represent an alkylenedioxy group with 1 or 2 carbon atoms,
with the proviso that if both substituents $R^4$ and $R^5$ represent oxygen containing radicals, these radicals are identical, and, if $R^1$, $R^2$ and/or $R^3$ represent hydroxy or lower alkylcarbonyloxy groups, the oxygen-containing radicals $R^4$ and/or $R^5$ are identical to these groups.
- $R^6$ represents an amino group disubstituted by lower alkyl, a pyridyl or pyrimidyl group, a 1-benzylpiperidin-4-yl group or group a

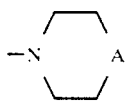  a wherein
- A represents a bond, a methylene group, oxygen or an N—$R^7$ group, wherein
- $R^7$ represents hydrogen, lower alkyl, a pyridyl or pyrimidyl group or a benzyl or phenyl group optionally substituted by lower alkyl or halogen,
- Z represents a Y—$(CH_2)_n$ group, wherein Y represents an N—$R^8$ group, wherein $R^8$ is hydrogen or lower alkyl, or, if none of the groups $R^1$-$R^5$ is hydroxy or lower alkylcarbonyloxy, Y also represents oxygen, and
- n represents a whole number of 2 to 4 or, if $R^6$ is a 1-benzylpiperidin-4-yl group, also represents zero, or Z also represents a bond, if $R^6$ stands for a group a, wherein A is an N—$R^7$ group,
and N-oxides and/or acid addition salts of compounds of Formula I.

If in the compounds of Formula I the substituents represent or contain lower alkyl groups, these may be straight chain or branched and contain in particular 1 to 4, preferably 1 or 2 carbon atoms. If the substituents represent or contain halogen, this is preferably fluorine, chlorine or bromine, most preferably chlorine.

The substituents $R^1$ to $R^3$ in the B-ring of the flavone structure preferably represent hydrogen or an oxygen-containing radical. Alkoxy groups —$OR^9$ may be straight chain or branched and contain 1 to 20, preferably 1 to 4, carbon atoms and most preferably represent methoxy groups. Alkenyloxy groups —O—$R^9$ may likewise be straight chain or branched and contain 3 to 20, preferably 3 or 4 carbon atoms, the double bond being separated from the oxygen atom by at least one carbon atom. In lower alkylcarbonyloxy groups $R^1$-$R^3$ the alkyl group may be straight chain or branched and contain 1 to 4, preferably 1 or 2 carbon atoms. Preferably the alkanoyloxy groups $R^1$-$R^3$ represent acetoxy. Preferably 2 or 3 of the substituents $R^1$ to $R^3$ represent methoxy or hydroxy.

The foregoing statements regarding the substituents of the B ring of the flavone structure likewise apply to the $R^4$ and $R^5$ substituents of the A ring. $R^4$ and $R^5$ preferably represent hydrogen. If oxygen-containing substituents are contained both in the A ring and in the B ring, these substituents are advantageously identical.

Pyridyl and pyrimidyl groups $R^7$ or $R^8$ contained in the $R^6$ group are never bonded by their nitrogen atoms. Preferably these groups are connected by the carbon atom in the 2-position. If Z represents a Y—$(CH_2)_n$ group, Y preferably represents an N—$R^8$ group, wherein $R^8$ preferably represents hydrogen. If $R^8$ stands for lower alkyl, this may be straight chain or branched and preferably represents methyl. If $R^6$ represents amino disubstituted by alkyl, the alkyl groups contained in $R^6$ contain 1 to 4, preferably 1 or 2 carbon atoms. If $R^6$ stands for a heterocycle a, A preferably represents an $R^7$-N< group. If $R^7$ contains or represents a phenyl ring, this may be unsubstituted, or mono-, di- or trisubstituted. Preferably $R^6$ represents a piperazine ring, substituted by a cyclic group, particularly a pyridyl group.

According to the invention, the new flavone-3-carboxylic acid compounds of Formula I and their acid addition salts and/or N-oxides, can be obtained in a known way in that (a) to prepare compounds of general Formula Ia,

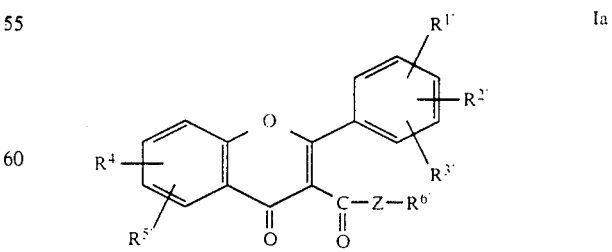

Ia wherein $R^{1'}$, $R^{2'}$, $R^{3'}$, $R^{4'}$, and $R^{5'}$, have the meanings given for $R^1$, $R^2$, $R^3$, $R^4$ and $R^5$ except for lower alkylcarbonyloxy, Z has the above meaning and $R^{6'}$ has the meaning given for $R^6$ with the exception of those groups in which $R^7$ represents hydrogen, reactive derivatives of acids of general Formula II,

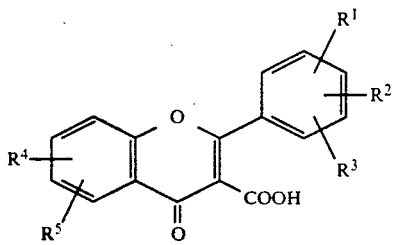

wherein $R^1$, $R^2$, $R^3$, $R^4$ and $R^5$ have the above meaning, but any hydroxy groups are provided with a protective group, are reacted with compounds of general Formula III,

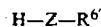  H—Z—R$^{6'}$   III wherein $R^6$, and Z have the above meaning, or
(b) to prepare compounds of general Formula Ib,

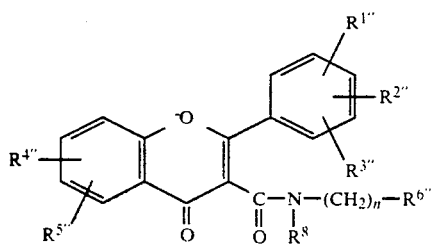

wherein n and $R^8$ have the above meanings, $R^{1''}$, $R^{2''}$, $R^{3''}$, $R^{4''}$ and $R^{5''}$ have the meanings given for $R^1$, $R^2$, $R^3$, $R^4$ and $R^5$ except for hydroxy and lower alkylcarbonyloxy, and $R^{6''}$ represents an amino group disubstituted with lower alkyl or the above defined group a, compounds of general Formula IV,

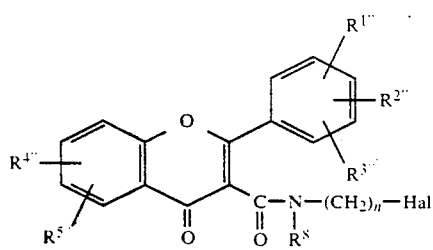

wherein $R^{1''}$, $R^{2''}$, $R^{3''}$, $R^{4''}$, $R^{5''}$, n and $R^8$ have the above meanings, and Hal represents halogen, are reacted with amines of general Formula V,

  H—R$^{6''}$   V wherein $R^{6''}$ has the above meaning, and if desired for preparing compounds of Formula I, wherein $R^1$, $R^2$, $R^3$, $R^4$ and/or $R^5$ represent lower alkylcarbonyloxy groups, in compounds of Formula Ia, wherein $R^{1'}$, $R^{2'}$, $R^{3'}$, $R^{4'}$ and/or $R^{5'}$ represents free hydroxy groups, these are acylated to lower alkylcarbonyloxy groups and/or if desired for preparing compounds of Formula I, wherein $R^1$, $R^2$, $R^3$, $R^4$ and/or $R^5$ represent free hydroxy groups, in compounds of Formula I, wherein $R^1$, $R^2$, $R^3$, $R^4$ and-/or $R^5$ represent lower alkoxy groups, these are converted into free hydroxy groups and/or for preparing compounds of Formula I, wherein $R^7$ represents hydrogen, from compounds of Formula I, wherein $R^7$ represents benzyl, the benzyl group is split off, and, if desired, compounds of general Formula I are oxidized to their N-oxides and/or converted into acid addition salts or the acid addition salts are converted into the free compounds.

The reaction of reactive derivatives of the acids of Formula II with amines or alcohols of Formula III according to process variant (a) may be performed using conventional acylation methods to form amides and esters. The acids are thereby activated in a known manner by conversion into a reactive derivative, for instance, mixed anhydrides, e.g. anhydrides with lower alkane carboxylic acids or lower alkyl sulfonic acids, particularly acetic acid or methane sulfonic acid, or acid halides, particularly chlorides or bromides, are considered as reactive acid derivatives. For example acid derivatives of Formula VI,

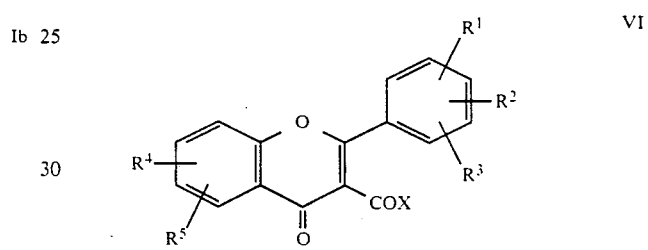

are suitable in which $R^1$ to $R^5$ have the above meanings and X represents halogen or an acyloxy group —OX', in which X' stands for lower alkylcarbonyl or lower alkylsulfonyl.

If in the acids of Formula II the substituents $R^1$, $R^2$, $R^3$, $R^4$, and/or $R^5$ represent free hydroxy groups, they must be protected during the reaction with the compounds of Formula III in a known manner by a protective group which can easily be split off again. For instance, acyl groups, e.g. lower alkanoyl groups such as acetyl groups, are suitable as protective groups. Protective acyl groups are advantageously introduced before the acids of Formula II are converted into their reactive derivatives. In preparing mixed anhydrides with lower alkane carboxylic acids the introduction of the protective groups may also occur simultaneously with the formation of anhydride.

The conversion of the free acids of Formula II into reactive acid derivatives occurs in a known manner. Thus acid halides of Formula VI may be obtained, e.g by reacting the acids with an acid halide, for instance phosphorus trichloride, phosphorus pentachloride, phosphorus tribromide, thionyl chloride or oxalyl chloride. If desired, the reaction may be performed in the presence of pyridine or another tertiary organic base. Mixed acid anhydrides may be obtained, e.g. by reacting acids of Formula II or their alkali metal salts with an appropriate organic acid chloride in an organic solvent which is inert under the reaction conditions, for instance a halogenated hydrocarbon, optionally in the presence of a tertiary organic base, for instance pyridine. In such a case any free hydroxy substituents of acids of Formula II are likewise acylated and thus provided with the protective group necessary for the subsequent reaction.

The reaction of the acid derivatives of Formula VI with the compounds of Formula III may take place in a solvent which is inert under the reaction conditions at temperatures between −30° C. and the boiling temperature of the solvent, preferably temperatures between −20° C. and room temperature. Halogenated hydrocarbons such as methylene chloride or chloroform, aromatic hydrocarbons such as benzene or toluene, cyclic ethers such as tetrahydrofuran or dioxane, or mixtures of these solvents are suitable as solvents. If necessary the reaction may be performed in the presence of an acid-binding reagent Inorganic bases, particularly alkali metal carbonates and hydroxides, and organic bases, particularly tertiary lower alkylamines and pyridines, e.g. triethylamine, pyridine, 4-dimethylaminopyridine or 4-pyrrolidinopyridine are examples of suitable acid-binding agents. Instead of an additional base, a surplus of an amine of Formula III may also be used. Organic bases used in surplus may also be used simultaneously as solvents.

Any protective acyl groups for hydroxy substituents are split off during reaction or in the course of working up and the hydroxy substituents are again released.

Advantageously the activation of acids of Formula II by conversion into a mixed anhydride may take place in situ in an inert organic solvent, for instance a halogenated hydrocarbon, and then the resulting mixed anhydride may be further reacted directly with the compound of Formula III.

The reaction of the acid of Formula II with the compound of Formula III can also be performed advantageously in the presence of a coupling reagent known from peptide chemistry to be suitable for activating acids for forming amides. In particular, alkyl, preferably cycloalkylcarbodiimides, preferably dicyclohexylcarbodiimide, carbonyldiimidazole and N-lower alkyl-2-halo pyridinium salts, particularly halides or tosylates, preferably N-methyl-2-chloropyridinium iodide (see e.g. Mukayama in Angew. Chemie 91, 789–812) are examples of suitable coupling reagents, which encourage the reaction by reacting with the acid in situ to form a reactive acid derivative. The reaction in the presence of a coupling reagent may be performed advantageously at temperatures from −30° C. to +30° C. using solvents such as halogenated hydrocarbons and/or aromatic solvents, if need be in the presence of an acid-binding amine.

The reaction of compounds of Formula IV with amines of Formula V according to process variant (b) may take place in a known manner under usual conditions for alkylating amines. The halogen substituent Hal in the compounds of Formula IV may stand for chlorine, bromine or iodine, preferably bromine. Advantageously the reaction is carried out in an organic solvent which is inert under the reaction conditions at temperatures between room temperature and the boiling temperature of the solvent. Dimethylformamide, aromatic hydrocarbons such as benzene or toluene, or halogenated hydrocarbons such as dichloromethane are examples of suitable solvents. If desired, the reaction may be carried out under addition of an organic or inorganic base. However, a surplus of the amine of Formula V may also be used and this may serve as an internal base. If chlorides or bromides of Formula IV are used, iodide ions in the form of an iodide salt, for example potassium iodide, may be added to speed up the reaction.

If the compounds of Formula Ia obtained contain free hydroxy groups $R^{1'}$, $R^{2'}$, $R^{3'}$, $R^{4'}$ and/or $R^{5'}$, these may be acylated in a known manner, if desired, to lower alkylcarbonyloxy groups. The acylation takes place according to the usual methods for forming esters by acylation, e.g. by reacting with reactive derivatives of the acids of Formula VII,

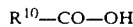

$$R^{10}-CO-OH \qquad VII$$

wherein $R^{10}$ represents lower alkyl. In particular halides and anhydrides of the acids of Formula VII are suitable as reactive derivatives. The reaction may take place under the conditions given above for reacting reactive derivatives of the acids of Formula II with compounds of Formula III.

Compounds of Formula I, wherein $R^1$, $R^2$, $R^3$, $R^4$ and/or $R^5$ represent free hydroxy, may advantageously be produced by cleavage of ether groups from appropriate compounds of Formula I, wherein $R^1$, $R^2$, $R^3$, $R^4$ and $R^5$ represent lower alkoxy, particularly methoxy. The freeing of the hydroxy groups may take place according to usual methods for phenol ether cleavage. For example, ether cleavage by treating the compounds with Lewis acids, particularly boron tribromide or trimethylsilyl iodide in a solvent which is inert under the reaction conditions, for example a halogenated hydrocarbon, at a temperature between −100° C. and +50° C., preferably between 0° C. and room temperature, is favorable.

For preparing compounds of Formula I, wherein $R^7$ represents hydrogen, from appropriate compounds of Formula I, wherein $R^7$ represents an optionally substituted benzyl group, the latter can be split off in a known way using hydrogenolysis.

The hydrogenolysis may take place with hydrogen using palladium/carbon as a catalyst in an organic polar solvent, for instance a lower alcohol in the presence of an acid which is stable under the reaction conditions, for instance a halogen hydracid.

The compounds of Formula I may be oxidized in a known manner to their corresponding N-oxides. The oxidation may take place e.g. with hydrogen peroxide or preferably with organic peracids in an organic solvent which is inert under the reaction conditions, for instance according to the method described in Chem. Rev. 68, 747 (1968). In particular, perbenzoic acids, e.g. 3-chloroperbenzoic acid, are suitable as oxidizing agents. For example, halogenated hydrocarbons such as dichloromethane are suitable as solvents. If the compounds contain several basic centers, the nitrogen atoms of all these centers may be oxidized.

The compounds of Formula I may be isolated from the reaction mixture and purified in a known manner. Acid addition salts may be converted in the usual way into the free bases and these converted in a known way into pharmacologically compatible acid addition salts if desired. If the compounds of Formula I contain several basic centers, they may form acid addition salts with only one or with several equivalents of acid.

As pharmacologically acceptable acid addition salts of the compounds I, for instance, their salts with inorganic acids such as hydrochloric acid, hydrobromic acid, sulfuric acid, phosphoric acid or organic acids such as tartaric acid, benzoic acid, acetic acid, lactic acid, citric acid, maleic acid, fumaric acid, malic acid, lower alkane sulfonic acids, benzene sulfonic acids or toluene sulfonic acids are suitable.

The flavone-3-carboxylic acids of Formula II used as starting products, wherein hydroxy substituents may be protected if desired by acyl, particularly lower alkylcarbonyl, and their salts, except for 3-flavonecarboxylic acid, 2'-methoxy-3-flavone-carboxylic acid and 5,7-dimethyl-3-flavonecarboxylic acid, have not previously been described in the literature and represent valuable new intermediate products for preparing pharmacologically active compounds, for instance the compounds of Formula I.

Acids of Formula IIa

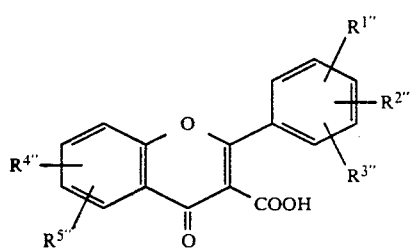

wherein $R^{1''}$, $R^{2''}$, $R^{3''}$, $R^{4''}$ and/or $R^{5''}$ have the above meanings, can be obtained in a known manner starting from appropriate flavones of Formula VIII

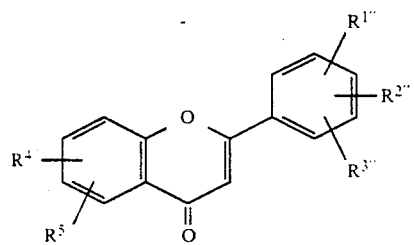

wherein $R^{1''}$, $R^{2''}$, $R^{3''}$, $R^{4''}$ and $R^{5''}$ have the above meanings.

The flavones of Formula VIII are first lithiated in the 3-position by reacting with nucleophile-free organic lithium bases and by treating the lithiated intermediate product of Formula IX

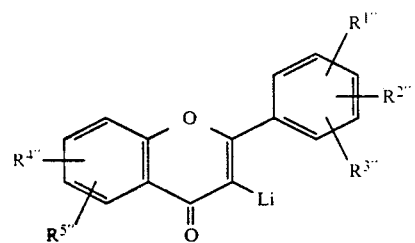

wherein $R^{1''}$, $R^{2''}$, $R^{3''}$, $R^{4''}$ and $R^{5''}$ have the above meanings, with carbon dioxide, whereby the lithium is then replaced by the carboxyl group. In particular, preferably lithium diisopropylamide or also lithium tetramethylpiperidide or lithium hexamethyldisilazide are organic lithium bases suitable as lithiating agents. The lithiation is carried out in a solvent which is inert under the reaction conditions, for instance a cyclic ether such as tetrahydrofuran, at temperatures between $-100°$ C. and $-30°$ C., preferably temperatures between $-90°$ C. and $-50°$ C. The resulting 3-lithio-flavone compounds are processed further directly into the acids of Formula IIa by treating the reaction solution with carbon dioxide and then acidifying it. Advantageously the reaction takes place with carbon dioxide at temperatures between $-100°$ C. and $-30°$ C. in a solvent which is inert under the reaction conditions, for instance a cyclic ether such as tetrahydrofuran. The carbon dioxide may be added to the reaction solution in the form of crushed dry ice or in the form of carbon dioxide gas.

For preparing acids of Formula II, wherein the substituents $R^1$, $R^2$, $R^3$, $R^4$ and/or $R^5$ represent hydroxy, appropriate methoxy-substituted acids of Formula II may be demethylated. The demethylation may be carried out according to processes usual for cleaving phenyl ether, for instance under the conditions given above for the preparation of compounds of Formula I containing free hydroxy substituents from appropriate lower alkoxysubstituted compounds of Formula I.

For preparing acids of Formula II, wherein hydroxy substituents $R^1$, $R^2$, $R^3$, $R^4$ and/or $R^5$ are protected by lower alkanoyl groups, preferably acetyl groups, the corresponding acids substituted by free hydroxy groups may be acylated in a known manner by reacting with halides or anhydrides of the corresponding lower alkane carboxylic acids, for instance alkane carboxylic acids with 1 to 4 carbon atoms in the alkane chain.

Compounds of Formula IV have not previously been described in the literature and represent valuable intermediate products for preparing pharmacologically active compounds, for instance compounds of Formula I.

Compounds of Formula IV can be obtained by reacting reactive derivatives of acids of Formula IIa with aminoalcohols of Formula X,

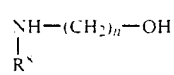

wherein $R^{10}$ and n have the above meanings, to form compounds of Formula XI

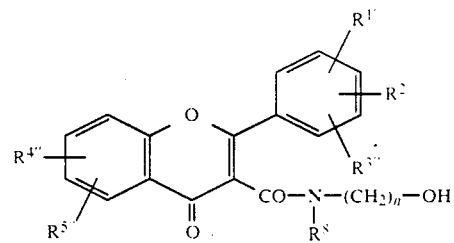

wherein $R^{1''}$, $R^{2''}$, $R^{3''}$, $R^{4''}$, $R^{5''}$, $R^8$ and n have the above meanings, and then replacing the hydroxy group in a known manner by halogen by reacting with phosphorus halides. The reaction of the reactive derivatives of the acids of Formula IIa with the aminoalcohols of Formula X may be carried out according to usual methods for forming amides by aminoacylation, for instance under the reaction conditions given above for the reaction of the reactive derivatives of the acids of Formula II with the compounds of Formula III.

The flavone compounds of Formula VIII are known or may be prepared according to known methods. For instance, flavones of Formula VIII may be obtained in a known manner by reacting 2-hydroxyacetophenone compounds of Formula XII

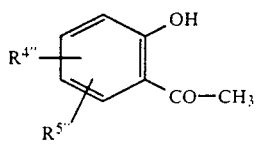

wherein $R^{4''}$ and $R^{5''}$ have the above meanings, first with benzoyl chloride compounds of Formula XIII

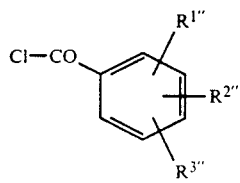

wherein $R^{1''}$, $R^{2''}$ and $R^{3''}$ have the above meanings, to form benzoic acid ester compounds of Formula XIV

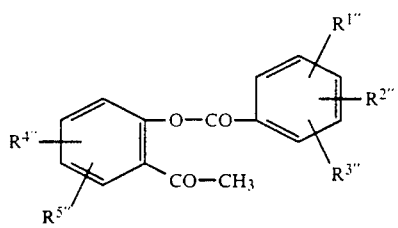

wherein $R^{1''}$, $R^{2''}$, $R^{3''}$, $R^{4''}$ and $R^{5''}$ have the above meanings, and then rearranging these by treating with strong bases to form compounds of Formula XV

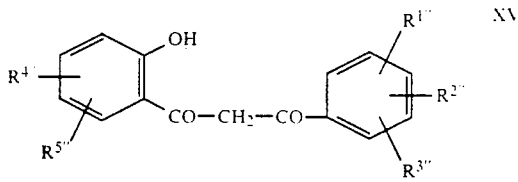

wherein $R^{1''}$, $R^{2''}$, $R^{3''}$, $R^{4''}$ and $R^{5''}$ have the above meanings, which themselves are cyclized with the elimination of water to form the flavones of Formula VIII.

The reaction of the 2-hydroxyacetophenones of Formula XII with the benzoyl chlorides of Formula XIII is carried out in a solvent which is inert under the reaction conditions in the presence of a quantity of a nonnucleophilic organic base sufficient to bind the hydrochloric acid formed at temperatures between room temperature and reflux temperature of the solvent, preferably temperatures between room temperature and 80° C. Tertiary amines such as pyridine or triethylamine, which can also act simultaneously as solvents, are suitable as organic bases. Halogenated hydrocarbons are suitable as further organic solvents. The resulting benzoic acid esters are then converted in a known manner by a Baker-Venkataraman rearrangement into the diketone compounds of Formula XV. The rearrangement can take place in a solvent which is inert under the reaction conditions, preferably pyridine, by treating with a strong base, for instance alkali metal hydroxide, which is suspended in the reaction solution, at temperatures between approximately 0° C. and room temperature. The subsequent cyclization of the diketone compounds of Formula XV is advantageously carried out in an acid medium in the presence of a reagent which causes water to be split off at a high temperature, preferably the boiling temperature of the reaction mixture. For instance, cyclization in a glacial acetic acid/sulfuric acid solution is favorable.

Flavone compounds of Formula VIII, wherein $R^{1''}$, $R^{2''}$, $R^{3''}$, $R^{4''}$ and/or $R^{5''}$ form an $R^9$—O group, may be obtained if desired by etherifying corresponding hydroxy-substituted flavones by reacting them with compounds of Formula XVI $$R^9 X \qquad \qquad XVI$$

wherein $R^9$ and Hal have the above meanings, under conditions suitable for forming phenol ethers. The etherification of hydroxy flavones is used in particular to introduce longer chains of $R^9$—O groups. The hydroxy flavones are known and/or can be produced if desired by demethylation of corresponding methoxy flavones.

The compounds of Formula III are known or may be obtained according to known methods.

The compounds of Formula I and their pharmacologically acceptable acid addition salts have interesting pharmacological properties, particularly inflammation-inhibiting, anti-allergic and edemainhibiting properties and are distinguished by a favorable activity profile with oral effectiveness, good tolerance and low toxicity.

Thus the compounds have in particular an inhibitive effect on the formation of oxygen radicals by inflamed cells. It is known that activated inflamed cells release oxygen radicals and oxygen-containing molecules with high oxidation potential. All these reactive oxygen compounds are referred to hereafter under the term "oxygen radicals". Oxygen radicals are responsible, particularly in acute and chronic inflammation, in toxicity of various types of foreign substances, and in X-ray or radioactive radiation exposure, for the degradation of cells or tissue proteins and lipids. Substances which inhibit the oxygen radical-forming activity of inflamed cells thus have a preventive and inhibiting effect on illnesses associated with symptoms of inflammation and can inhibit the occurrence of cell damage caused by inflammation.

Furthermore, the compounds show a marked specific inhibition of lipoxygenase. The lipoxygenase enzyme controls the biosynthesis of biologically active mediators of the leucotriene type. It is known that leucotrienes play a decisive part in inducing inflammatory and allergic reactions in the human body and also, for instance, in the development of asthmatic illnesses. They can also have negative effects on cardiovascular activity. Lipoxygenase-inhibiting substances have a preventive and inhibiting effect on the symptoms of illnesses caused by mediators of the leucotriene type, which may occur e.g. in rheumatic, allergic and asthmatic illnesses. They are therefore useful in treating illnesses of this type.

Furthermore, the compounds also have edemainhibiting properties.

The properties of the compounds of Formula I of inhibiting lipoxygenase and of inhibiting the formation of oxygen radicals by inflamed cells can be shown by standard pharmacological experiments in vitro. The edema inhibiting properties are effectively demonstrated by standard pharmacological tests on animals

DESCRIPTION OF EXPERIMENTAL METHODS

1. To determine the inhibiting effect on the oxygen radical-forming activity of inflamed cells, the in vitro inhibition of the release of oxygen radicals from activated peritoneal exudate cells (=PEC) of mice was determined in the chemiluminescence (CL) test according to the method of Mueller-Peddinghaus (Int. J. Immunopharmac. 6, 455–466 (1984)). In this case the chemiluminescence produced by reacting the oxygen radicals contained in an activated PEC suspension with the chemiluminescence amplifier lucigenin (=10,10'-dimethyl-bis-9,9-acridinium nitrate) is measured. The intensity of the chemiluminescence is a measurement of the oxygen radical content in the suspension and thus the degree of activity of the inflamed cells. In this, three functionally different parameters are detected, the spontaneous CL, the induced CL and the peak CL. The spontaneous CL and the induced CL on the one hand and the peak CL on the other hand differ from each other because in the first two parameters the test substances are in contact with the cells for a 30 minute preincubation period before the inflammation irritant is added, whereas with the peak CL the cells are first stimulated, and the test substance is added at the peak of their activity. The measurement of the spontaneous CL thus detects the influence of the test substance on the relative rest activity of inflamed cells, the induced CL represents the effect of the test substances on the activatability of the cells and the inhibition of the peak CL indicates the effect of the test substances on the maximum activity of the inflamed cells.

1.1 Production of PEC suspension used in the test

In order to induce the PEC formation, female mice of 20–25 g body weight were each injected i.p. with 2 ml of a 3% solution of thioglycollate in sterile isotonic sodium chloride solution Twenty-four hours after the thioglycollate injection the cells, which predominantly consisted of polymorphonuclear leucocytes, were recovered by washing out of the abdominal cavity and washed twice. As cell culture medium there was added a commercially available solution under the designation RPMI 1640 (pH 7.2) (produced by Flow Laboratories, Meckenheim, Germany), which contains 10% fetal calf serum (FCS, produced by Seromed GmbH, Munich, Germany) 18 $\mu$mol/l sodium bicarbonate and 2 $\mu$mol/l L-glutamine. The cell pellets of four animals each time were resuspended in cell culture medium, collected together and the suspension was made up to $2 \times 10^6$ cells per ml with cell culture medium. The cell suspensions were kept under ice cooling until their use the same day.

1.2 Production of the complement opsonized zy-mosan (=ZyC$_3$b) suspension used for activation 200 mg zymosan (glycoprotein mixture isolated from the cell walls of brewer's yeast, Sacchomyces cerivisiae, produced by Sigma Chemical Co., Munich, Germany) were suspended in 10 ml phosphate buffer solution according to Dulbecco (produced by Flow Laboratories, Meckenheim, Germany), well stirred and heated for thirty minutes in a water bath to 100° C. After cooling, it was centrifuged for five minutes at 4° C. and at 600$\times$g and the supernatant was discarded. The sediment was resuspended in 50 ml human serum and incubated for thirty minutes at 37° C. in a shaking water bath. Then it was centrifuged for five minutes at 600 $\times$g and 4° C., the supernatant decanted and the sediment washed with phosphate buffer solution. The working suspension of $8 \times 10^{-3}$ g ZyC$_3$b/ml was produced from the sediment by dilution with phosphate buffer solution (Mueller-Peddinghaus et al., Zbl. Vet. Med. B. 30, 559–575).

1.3 Chemiluminescence (CL) measurement (Peak-CL)

The PEC suspension was divided into samples of 100 $\mu$l each, placed in test tubes, and these were incubated for ten minutes at a temperature of 37° C. in a measurement device (Chemiluminescence analyzer, Laboratorium Prof. Berthold, Wildbad, Germany). Then in order to amplify the chemiluminescence, 100 $\mu$l lucigenin solution was added (final concentration $1.54 \times 10^{-4}$ mol/l) and incubated for 16 more minutes. The cells were then activated by the addition of 100 $\mu$l of the ZyC$_3$b suspension produced as described in section 1.2 plus 100 $\mu$l phosphate buffer solution. The maximum activity of the cells is reached after sixteen minutes. At this point in time 100 $\mu$l of test substance (containing $10^{-4}$ Mol substance/l) were added and the reduction of the chemiluminescence signal due to the added substance was determined in relation to controls. The result was determined as a percentage of inhibition of the oxygen radical liberation.

1.4 Chemiluminescence measurement (spontaneous CL and induced CL)

The determination of the two parameters followed the same test principle as the measurement of the peak CL with the difference that 100 $\mu$l PEC-suspension together with 100 $\mu$l test substance solution were preincubated for thirty minutes at 37° C. in the measuring device. At the end of this preincubation phase, 100 $\mu$l lucigenin were added, and in the course of the subsequent sixteen minute incubation phase the spontaneous CL parameter was determined with two measuring points. Then 100 $\mu$l ZyC$_3$b + 100 $\mu$l phosphate buffer were added, and during the course of the subsequent twenty-four minute cell activation the induced CL parameter was measured with three measuring points.

All measurements were determined twice. The parameters spontaneous CL and induced CL were determined on the same day with two separate cell pools.

2. In order to investigate the lipoxygenase-inhibiting properties, the inhibiting effect of the substances on the biosynthesis of leucotriene B$_4$ (=LTB$_4$) from arachidonic acid by activated inflamed cells was determined in vitro. Leucotriene B$_4$, a dihydroxy fatty acid which plays an important role not only in the inflammation but also in allergic reactions was oxidatively formed, starting from arachidonic acid, by oxidation through the action of the enzyme lipoxygenase.

LTB$_4$ Synthesis and Inhibition Test

Polymorphonuclear leucocytes (PMNL) were purified in a known manner according to the method of Carlson and Kaneko (Proc. Soc. Exp. Med. 142, 853–856 (1973)). The cells were suspended in an incubation medium (pH 7.4) which consisted of 150 mM NaCl, 4 mM KCl, 2.5 mM Na$_2$HPO$_4$, 3.5 mM KH$_2$PO$_4$, 0.75 mM CaCl$_2$ and 5 mM glucose. Each sample contained $3 \times 10^7$ cells in a total volume of 2 ml medium and was preincubated for a period of thirty minutes at 37° C. with 10 $\mu$l 5 test substance solution ($10^{-4}$ Mol/l test substance dissolved in dimethyl-sulfoxide or ethanol). Then Ca-ionophore A 23187 (produced by Sigma Chem. Co., Munich, Germany) was added (10 mmol/l final concentration) and after a further twenty minutes arachidonic acid (produced by Sigma Chem. Co.) (final concentration $1.5 \times 10^{-5}$ mol/l) and calcium (final concentration $2 \times 10^{-3}$ mol/l) were added.

After a further 10 minutes at 37° C. the cells were centrifuged and the supernatant was extracted twice with diethyl ether. The combined extracts were evaporated under vacuum to dryness and the residue was taken up in 0.5 ml 30% aqueous methanol and was analyzed with the aid of high pressure liquid chromatography with phase reversal (=reversed phase-HPLC). The stationary phase (=separating medium) consisted of silica gel containing octadecyl groups chemically bound thereto (=RSIL C18 HP; produced by Autech, Darfield, IL.). The solvent mixture is methanol : water : acetic acid (67:33:0.1; v/v/v), which had been adjusted to a pH value of 6.2 with $NH_3/H_2O$. The flow velocity was 1 ml/min. The measurement of $LTB_4$ was carried out at 280 nm with a spectro-monitor III (LDC-Milton Ray, Riviera Beach, FL.) and the data were taken up and integrated by a Varian 4270 integrator (Varian, Palo Alto, CA.). The $LTB_4$ signals were compared with those of the control (cell incubation with solvent) and reported as percent inhibition of $LTB_4$ synthesis compared with the controls.

3. Determination of the minimum toxic dose

Male mice of 20 to 25 g weight were given maximal doses of 300 mg/kg of test substance per os. The animals were carefully watched over a period of three hours for toxicity symptoms. Over a period of twenty-four hours after administration, all symptoms and deaths were recorded. Associated symptoms were also watched and recorded. If death or strongly toxic symptoms were noted, further mice were given increasingly lower doses. The lowest dose which brought about death or strongly toxic symptoms was reported as the minimum toxic dose.

The following Table A shows the results obtained according to the previously described test methods. The example numbers given for the compounds of Formula I refer to the subsequent synthesis examples.

TABLE A

| Test Substance Example No. | Inhibition in vitro of the oxygen radical liberation in the Chemiluminescence Test % inhibition | | | Lipoxygenase inhib. in vitro % inhibition of the $LTB_4$ synthesis at $10^{-4}$ Mol/l | Minimal toxic dose mg/kg mouse p.o. |
|---|---|---|---|---|---|
| | Pk. CL | Spnt. CL | Ind. CL | | |
| 1c | 47 | 49 | 39 | 52 | >300 |
| 2b | 58 | 67 | 54 | 92 | >300 |
| 3b | 61 | 94 | 83 | 8 | 300 |
| 4e | 76 | 95 | 82 | 10 | 300 |
| 5 | 12 | 49 | 25 | | >300 |
| 7a | 68 | 75 | 65 | 38 | >300 |
| 7b | 44 | 61 | 50 | 42 | >300 |
| 14e | 99 | 98 | 99 | 86 | >300 |
| 18b | 41 | 30 | 50 | | 300 |
| 20b | 27 | 72 | 43 | | 100 |
| 22b | 25 | 67 | 43 | | 300 |
| 23 | 63 | 95 | 88 | | 300 |
| 24 | 1 | 55 | 14 | 46 | >300 |
| 26 | 10 | 13 | 3 | 43 | |
| 28 | 5 | 54 | 29 | | >300 |
| 29 | 75 | 65 | 74 | 97 | |
| 30 | 85 | 85 | 85 | 44 | >300 |
| 32b | 56 | 71 | 65 | 25 | >300 |
| 34 | 25 | 54 | 55 | 25 | |
| 35 | | | | 100 | |
| 39b | 99 | 99 | 99 | 93 | |
| 42b | 99 | 99 | 100 | 100 | |
| 46 | 11 | 52 | 25 | | >300 |

TABLE A-continued

| Test Substance Example No. | Inhibition in vitro of the oxygen radical liberation in the Chemiluminescence Test % inhibition | | | Lipoxygenase inhib. in vitro % inhibition of the $LTB_4$ synthesis at $10^{-4}$ Mol/l | Minimal toxic dose mg/kg mouse p.o. |
|---|---|---|---|---|---|
| | Pk. CL | Spnt. CL | Ind. CL | | |
| 47 | 70 | 78 | 76 | | 100 |
| 49 | 41 | 86 | 64 | | 300 |
| 53 | 77 | 73 | 83 | 77 | |
| 54 | 72 | 91 | 83 | 44 | >300 |
| 56 | 37 | 52 | 70 | | |
| 59 | 84 | 97 | 94 | | >300 |

The anti-edema properties of the compounds of Formula I can be demonstrated by their inhibition of local edema formation caused by injection of carrageenin in rats feet.

Description of the test method for determining the inhibition of the carrageenin foot edema in rats according to the method of Winter et al. (Proc. Soc. Exp. Biol. Med. 111, 544–547 (1962).

Male Wistar rats with a body weight of about 120 to 140 g were used. A dose of the test substance was suspended in a volume of 0.5 ml per 100 g body weight of a 1% Tylose solution (=methyl cellulose) and administered per os by means of an esophageal probe or injected i.p. A control group received only the Tylose solution. One hour later in order to initiate the inflammation, 0.1 ml of a 1% suspension of carrageenin (Satiagum E) in isotonic sodium chloride solution as irritant was injected intraplantary in the right hind foot. A similar volume of isotonic sodium chloride solution was injected in the left hind foot. The volume of the each rat's foot was measured plethysmometrically both before and two hours after administration of the irritant, and the swelling of the foot volume after the carrageenin application was compared to the foot which was treated only with sodium chloride solution. The inhibition of edema formation by the test substances in the treated animals was compared in percentage terms with the animals of the untreated control group.

The following Table B gives the results obtained with compounds of Formula I according to the aforedescribed methods.

TABLE B

| Test Substance Example No. | Dose μmol/kg | % Inhibition of Carrageenin foot edema |
|---|---|---|
| 1c | 100 p.o. | 44 |
| 1c | 215 i.p. | 55 |
| 2b | 100 p.o. | 25 |
| 4e | 215 p.o. | 50 |
| 4e | 215 i.p. | 54 |
| 6b | 215 i.p. | 75 |
| 7b | 215 p.o. | 40 |
| 10b | 215 p.o. | 30 |
| 10b | 215 i.p. | 35 |
| 143 | 215 i.p. | 33 |
| 16a | 100 p.o. | 20 |
| 25 | 215 p.o. | 25 |
| 25 | 215 i.p. | 58 |
| 34 | 215 p.o. | 30 |
| 39b | 215 i.p. | 62 |
| 36 | 215 p.o. | 30 |
| 52 | 215 i.p. | 53 |
| 53 | 215 i.p. | 50 |
| 54 | 215 i.p. | 40 |

As medicines, the compounds of Formula I, their N-oxides and their physiologically acceptable acid addition salts together with conventional pharmaceutical adjuvants can be contained in galenic preparations such as, for example, tablets, capsules, suppositories or solutions. These galenic preparations can be prepared according to known methods using conventional solid carrier materials such as, for example, lactose, starch or talc or liquid diluents such as, for example, water, fatty oils or liquid paraffins and using conventional pharmaceutical adjuvants, for example, tablet disintegrators, solubilizers or preservatives.

The following Examples serve to further illustrate the invention without, however, limiting its scope in any way.

EXAMPLE 1

3-{[4-(2-Pyridyl)-piperazin-1-yl]-carbonyl}flavone (a) To produce a mixed anhydride, 6 g flavone-3-carboxylic acid were dissolved in 50 ml absolute dichloromethane and cooled to −20° C. with the exclusion of moisture. In direct succession 5.5g dimethylaminopyridine and 2.2 ml methanesulfonyl chloride were introduced into the cooled mixture.

(b) To the reaction solution containing mixed anhydride produced in step (a), 3.3 g of 1-(2-pyridyl)piperazine were added over ten minutes. The reaction mixture was stirred for thirty minutes at −20° C. and for a further two hours at room temperature. The reaction mixture was then worked up by pouring into 100 ml of saturated sodium bicarbonate solution and shaken. The organic phase was separated, dried over sodium sulfate and concentrated. 11.9 g of an oily crude product were obtained. This was purified by column chromatography on silica gel under slightly elevated pressure (flash chromatography) using ethyl acetate/methanol 7:3 as eluent. 9 g of crystalline crude product were obtained which were recrystallized again from ether. 5 g pure 3-{[4-(2-pyridyl)-piperazin-1-yl]-carbonyl}flavone were thereby obtained. Empirical formula: $C_{25}H_{21}N_3O_3$; molecular weight: 411.5: melting point 178°–181° C.

(c) For conversion into the hydrochloride, 2.1 g of the title compound were dissolved in dichloromethane, and the solution was treated with hydrogen chloride gas for about 5 minutes under ice cooling. Then it was evaporated to dryness, and the residual crystals were taken up in diethyl ether, stirred for a while and filtered with suction. 2.19 g of the monohydrochloride of the title compound were obtained which crystallized as the dihydrate. Empirical formula: $C_{25}H_{21}N_3O_3 \cdot HCl \cdot 2H_2O$; Molecular Weight 484; Melting point 135°–139° C.

EXAMPLE 2

3-[(4-Benzyl-piperazin-1-yl)-carbonyl]flavone (a) 6 g of flavone-3-carboxylic acid was converted into the mixed anhydride with 5.5 g 4-dimethylaminopyridine and 2.2 ml methanesulfonyl chloride in 50 ml absolute dichloromethane under the conditions described in Example 1 (a), and the mixed anhydride was then reacted with 4.42 ml N-benzylpiperazine as described in Example 1(b). The working up of the reaction mixture and the purification of the resulting crude title compound were carried out in the manner described in Example 1 (b). 9 g of 3-[(4-benzylpiperazin-1-yl)-carbonyl] flavone were obtained.

Empirical formula: $C_{27}H_{24}N_2O_3$, Molecular weight 424.5; Melting point 149°–150° C.

(b) Two g of the title compound was dissolved in ethanol and mixed with a solution of 0.27 g (=1 equivalent) L(+)-tartaric acid in ethanol in order to convert it into the monotartrate salt. The mixture was concentrated whereby the 3-[(4-benzyl-piperazin-1-yl)-carbonyl] flavone tartrate monohydrate crystallized out. 2.4 g of the pure tartrate were obtained.

Empirical formula: $C_{31}H_{30}N_2O_9 \cdot 1H_2O$; Molecular weight 592.6; melting point 117°–120° C.

EXAMPLE 3

3-[3-(Diethylamino)-propoxycarbonyl] flavone (a) To produce a mixed anhydride, 4.0 g flavone-3-carboxylic acid were dissolved in 100 ml dichloromethane, reacted with 3.67 g dimethylaminopyridine and cooled to −20° C. 1.28 ml of methanesulfonyl chloride were added to the cooled solution, and the reaction mixture was stirred for 10 minutes.

(b) To the cooled reaction mixture containing mixed anhydride produced in step (a) were added 1.28 ml 3-diethylaminopropan-1-ol, and the reaction mixture was allowed to react for two hours at room temperature. The reaction mixture was subsequently worked up by shaking it with saturated sodium bicarbonate solution, the organic phase was separated, washed with water, dried over sodium sulfate and concentrated. The crude product, still contaminated with diethylaminopyridine, was purified by column chromatography on silica gel under slightly elevated pressure (flash chromatography) using methyl ethyl ketone/diethylamine 30:1 as eluent. 4.94 g of an oily crude product were obtained. For further purification this was dissolved in ether, the ether solution shaken with 1N aqueous hydrochloric acid solution, the aqueous phase was separated, neutralized with sodium bicarbonate solution and shaken with ether. The ether phase was thereafter washed with water, dried over sodium sulfate and concentrated. 4.0 g of the title compound were obtained as an oil.

For conversion into the hydrochloride, 3.7 g of the title compound obtained above were dissolved in absolute dichloromethane, and the solution was treated with hydrogen chloride gas. Subsequently the solution was concentrated whereupon the chloride of the title compound crystallized out. 3.8 g of 3-[3-(diethylamino)-propoxycarbonyl] flavone hydrochloride were obtained.

Empirical formula: $C_{23}H_{26}NO_4Cl$; Molecular weight 415.92; Melting point 173°–179° C.

EXAMPLE 4

3-{4-[4-(2-Pyridyl)-[piperazin-1-yl]-butylaminocarbonyl} flavone (a) 28.1 ml 1-(2-Pyridyl)-piperazine and 55.3 ml 1,4-dibromobutane were dissolved in 150 ml of isopropanol, and 16.6 g sodium carbonate was suspended in the solution. It was subsequently filtered, the filtrate concentrated by ⅓ in a rotary evaporator and cooled for twelve hours in a refrigerator. Then the spirobutylpiperazinium bromide which had crystallized out was suction filtered, washed with ether and dried. 52.9 g of the spirobutylpiperazinium bromide were obtained.

(b) 30 g of the spirobutylpiperazinium bromide obtained above were dissolved in 400 ml absolute dimethylformamide and reacted with 13.3 g sodium azide. The reaction mixture was heated for eight hours under reflux. After cooling, the mixture was mixed with an equal volume of diethyl ether and shaken with saturated sodium carbonate solution. The ether phase was separated, the aqueous sodium bicarbonate solution was subsequently extracted twice, and the combined ether phases were dried over sodium sulfate and concentrated. 17.3 g of 4-(4-azidobutyl)-1-(2-pyridyl)-piperazine were obtained as a brownish-red oil. The product was used without further purification.

(c) 17.3 g of the azide compound obtained above were dissolved in 300 ml methanol. The solution was mixed with 10 g Raney nickel and the azide was hydrogenated to the corresponding amine under a hydrogen pressure of 3 bar. At the end of the hydrogenation, the Raney nickel was removed by suction filtering, washed with methanol and the combined methanol phases were concentrated. There remained 14.2 g of an oily crude product which partially crystallized. After separating the crystals, the remainder of the crude product was purified by column chromatography on silica gel under slightly elevated pressure using methanol/triethylamine 30:2. There were obtained 12.9 g 4-[4-(2-pyridyl)piperazin-1-yl]-butylamine, Melting point 161°–168° C.

(d) 3.6 g of the 4-[4-(2-pyridyl)-piperazin-1-yl]butylamine obtained above were added to a reaction mixture cooled to −20° C. which contained, in 100 ml of absolute dichloromethane, a mixed anhydride produced in a manner analogous to Example 1 (a) from 4.0 g flavone-3-carboxylic acid, 3.367 g dimethylaminopyridine and 1.28 ml methanesulfonyl chloride. The reaction mixture was allowed to warm up to room temperature and stirred at room temperature for two hours. Subsequently the reaction mixture was worked up analogously to Example 3, and the resulting title compound was recrystallized from ethylacetate. There were obtained 4.7 g 3-{4-[4-(2-pyridyl)-piperazin-1-yl]-butylaminocarbonyl)-flavone. yl]-butylaminocarbonyl}-flavone.

Empirical formula $C_{29}H_{30}N_4O_3$; molecular weight 482.59; melting point 170°–176° C.

(e) The title compound was reacted with hydrogen chloride gas under the conditions described in Example 1 (c). The amorphous trihydrochloride of the title compound was obtained.

Empirical formula: $C_{29}H_{33}N_4O_3Cl_3$. 3.34 $H_2O$, molecular weight 652.17.

EXAMPLE 5

3-[(4-Benzylpiperazin-1-yl-carbonyl]-flavone N-oxide

3-[(4-Benzylpiperazin-1-yl)-carbonyl] flavone produced in accordance with Example 2 was dissolved in 50 ml dichloromethane and reacted with 1.4 g m-chloroperbenzoic acid. The reaction mixture was stirred for one hour at room temperature, whereby the N-oxidation occurred to completeness. For working up, the reaction mixture was then concentrated, the residue dissolved in methanol and reacted with two spoonfuls of strongly basic anion exchanger (commercial products "Merck III" produced by Merck & Co. or "Amberlite IRA 400", produced by Rohm and Haas) and stirred for about two hours. It was then filtered, the filtrate was concentrated and the residual crude product was taken up in ether. After a time the product crystallized. 2.95 g of the title compound were obtained.

Empirical formula: $C_{27}H_{24}N_2O_4$. 2.1 $H_2O$; Molecular weight 440.5; Melting point 194°–196° C.

EXAMPLE 6

3′,4′,5′-Trimethoxy-3-{4-[4-(2-pyridyl)-piperazin-1-yl]-butylaminocarbonyl}-flavone (a) 32.6 g of 3,4,5-Trimethoxybenzoylchloride were dissolved in 50 ml pyridine; 17 ml of 2-hydroxyacetophenone were added to the solution with stirring, and the reaction mixture was heated for one hour to 80° C. After cooling, the mixture was worked up by pouring on to a mixture of 45 ml of 37% hydrochloric acid, 45 ml water and 500 g ice. The product which precipitated was filtered, washed to neutrality with water and dried. 44.7 g of the 2′-methylcarbonylphenyl ester of 3,4,5-trimethoxybenzoic acid were obtained which was reacted further without purification.

(b) For the Baker-Venkataraman rearrangement, a solution of the benzoic acid ester obtained in step (a) in 80 ml pyridine was added under cooling with ice to a suspension of 42.5 g of finely divided sodium hydroxide in 50 ml absolute pyridine. The cooling bath was removed and the reaction mixture was vigorously stirred. After two hours the reaction mixture was worked up by pouring it into a mixture of 350 ml concentrated hydrochloric acid and 750 ml of crushed ice. The yellow colored product precipitated out and was suction filtered, washed to neutrality with water and dried. 42.6 g of 2-hydroxy-3′,4′,5′-trimethoxybenzoylacetophenone which was immediately further processed.

(c) 42.6 g of the diketone obtained above were reacted with 150 ml glacial acetic acid and 5.7 ml of concentrated sulfuric acid, and the reaction mixture was heated for one and half hours to 120° C. After cooling, the mixture was worked up by pouring it onto 500 g of ice and stirring vigorously, whereby the 3′, 4′, 540-trimethoxyflavone which was formed crystallized. It was filtered, washed with water and dried. 38.9 g of 3′, 4′,5′-trimethoxyflavone were obtained which could be directly further processed.

(d) 9.9 ml Diisopropylamine were reacted with 12 ml tetrahydrofuran under a nitrogen atmosphere, and 44.5 ml 1.6 n butyllithium/n-hexane were added at 0° C. to this mixture, and the mixture was cooled to −60° C. Then a further 50 ml of absolute tetrahydrofuran were added, and the solution was cooled to −78° C. A solution of 15 g 3′,4′,5′-trimethoxyflavone in 500 ml of absolute tetrahydrofuran cooled to about −60° C. was then quickly added to the lithium diisopropylamide solution. After three minutes 10 g of freshly crushed dry ice ($CO_2$, −78° C.) were added. Then the cooling was removed, and the mixture was allowed to warm to room temperature, excess gaseous carbon dioxide being stirred out of the solution. The reaction mixture was worked up by adjusting to pH1 with half-concentrated hydrochloric acid and extracted with dichloromethane. The dichloromethane phase was shaken with an aqueous saturated sodium bicarbonate solution (about 100 ml). The aqueous phase was separated and carefully brought to pH1 with concentrated hydrochloric acid, whereby the resulting 3′,4′,5′-trimethoxyflavone-3-carboxylic acid precipitated out. The precipitated product was extracted from the reaction mixture with dichloromethane. The dichloromethane phase was separated, dried over sodium sulfate and concentrated, whereupon the product crystallized. 14.75 g of 3′,4′,5′-trimethoxyflavone-3-carboxylic acid were obtained.

Empirical formula $C_{19}H_{16}O_7$; Molecular weight: 356.34; Melting point: 260°–262° C.

(e) Under the conditions described in Example 1 (a) 3.6 g 3',4',5'-trimethoxyflavone-3-carboxylic acid were converted with 2.1 g 4-dimethylaminopyridine and 0.72 ml mesyl chloride in 100 ml absolute dichloromethane into the mixed anhydride, and this was then reacted under the conditions described in Example 4 (d) with 2.2 g of 4-[4-(2-pyridyl)-piperazin-1-yl]-butylamine. The reaction mixture was then worked up analogously to Example 4 (d). 3.4 g of 3',4',5'-trimethoxy-3-{4-[4-(2-pyridyl)-piperazin-1-yl]-butylaminocarbonyl}-flavone were obtained.

Empirical formula: $C_{32}H_{36}N_4O_6$, Molecular weight: 572.67; Melting point: 168°–173° C.

(f) The title compound was reacted with hydrogen chloride gas following the procedure of Example 1 (c). The amorphous monohydrochloride of the title compound was obtained.

Empirical formula: $C_{32}H_{36}N_4O_6 \cdot 2.2\ HCl \cdot 3\ H_2O$; molecular weight: 706.93.

EXAMPLE 7

3',4',5'-Trimethoxy-3-{[4-(2-pyridyl)-piperazin-1-yl]-carbonyl) flavone (a) 8 g of 3',4',5'-trimethoxy-flavone-3-carboxylic acid with 5.5 g 4-dimethylaminopyridine and 2.2 ml mesylchloride in 100 ml absolute dichloromethane were converted into the mixed anhydride analogously to Example 1 (a), and this was then reacted with 3.6 g 1-(2-pyridyl)-piperazine analogously to Example 1 (b). The working up of the reaction mixture and the purification of the crude title compound obtained were carried out analogously to Example 1 (b). 7.5 g of 3',4',5'-trimethoxy-3-{[4-(2-pyridyl)-piperazin-1-yl]-carbonyl} flavone were obtained.

Empirical formula: $C_{28}H_{27}N_3O_6 \cdot 0.5H_2O$; Molecular weight: 510.55; Melting point: 90°–95° C.

(b) The title compound was reacted with hydrogen chloride gas analogously to Example 1 (c). The monohydrochloride was obtained.

Empirical formula: $C_{28}H_{28}N_3O_6Cl \cdot 1.5\ H_2O$; Molecular weight: 565.02; Melting point: 135°–140° C.

EXAMPLE 8

3',4',5'-Trimethoxy-3-[(4-benzylpiperazin-1-yl)-carbonyl] flavone (a) Under the conditions given in Example 1 (a), 6 g of 3',4',5'-trimethoxy-flavone-3-carboxylic acid with 4.1.g 4-dimethylaminopyridine and 1 6 ml mesylchloride in absolute dichloromethane were converted into the mixed anhydride. This was reacted with 3.3 ml 1-benzylpiperazine analogously to Example 1 (b). The reaction mixture was worked up analogously to Example 1 (b). 7.0 g of pure 3',4',5'-trimethoxy-3-[(4-benzyl-piperazin-1-yl)-carbonyl] flavone were obtained Empirical formula: $C_{30}H_{30}N_2O_6 \cdot 0.5H_2O$; Molecular weight: 523.58; Melting point: 195°–198° C.

(b) The title compound was reacted analogously to Example 1 (c) with hydrogen chloride gas. The monohydrochloride was obtained. Empirical formula: $C_{30}H_{31}N_2O_6Cl \cdot 1.5H_2O$; Molecular weight: 578.06; Melting point: 210°–214° C.

EXAMPLE 9

3',4',5'-Trihydroxy-3-{4-[4-(2-pyridyl)-piperazin-1-yl]-butylaminocarbonyl} flavone .

(a) 3.5 g of 3',4',5'-trimethoxy-3-{4-[4-(2-pyridyl)piperazin-1-yl]-butylaminocarbonyl} flavone (produced according to Example 7) were dissolved in 200 ml of dichloromethane The solution was cooled under a nitrogen atmosphere to 0° C. 43 ml of 1-molar boron tribromide solution in dichloromethane were added to the cooled solution. The reaction mixture was stirred for twelve hours during which it was allowed to warm to room temperature. For working up, the reaction mixture was then carefully reacted with water and neutralized to pH 7 with a saturated sodium bicarbonate solution. The title compound thereby precipitated out in contaminated form and was filtered out and dried at 80° C.

(b) For further purification the trihydroxy compound was converted into its triacetate. For this purpose 3g of the crude title compound were suspended in a mixture of 32 ml acetic anhydride, 32 ml pyridine and 50 ml dichloromethane, and the mixture was stirred until a substantially homogenous solution existed. Then the reaction mixture was shaken with ice water, and the organic phase was separated and dried over sodium sulfate. In order to remove pyridine residues, it was concentrated twice with additions of toluene. The remaining residue was purified by column chromatography on silica gel under slightly elevated pressure (flash chromatography) using tetrahydrofuran/dichloromethane 3:1 as the eluent. By this means pure 3',4',5'-triacetoxy-3-(4-[4-(2-pyridyl)-piperazin-1-yl]-butylaminocarbonyl} flavone was obtained.

(c) To produce the pure trihydroxy title compound, the purified triacetoxy compound obtained above was dissolved in absolute methanol, and the solution was reacted with three drops of triethylamine. Under these conditions a transesterification took place, the course of which was monitored by thin layer chromatography. As soon as no more triacetoxy compound could be detected by thin layer chromatography and the transesterification was complete, the reaction mixture is concentrated, the residue was shaken with water, filtered out and again washed with water. 1.0 g of the pure amorphous title compound were obtained.

Empirical formula: $C_{29}H_{30}N_4O_6$; Molecular weight: 530.59.

EXAMPLE 10

3',4',5'-trihydroxy-3-{[4-(2-pyridyl)-piperazin-1-yl]-carbonyl} flavone (a) 13.4 g of 3',4',5'-Trimethoxy-3-{[4-(2-pyridyl)piperazin-1-yl]-carbonyl} flavone (produced analogously to Example 6) were reacted with 107.2 ml of a 1 molar boron tribromide solution in dichloromethane as described in Example 9 (a). The reaction mixture was worked up in the manner described in Example 9 (a), whereby 9 g of dried crude product were obtained. This was converted to the triacetate of the title compound in the manner described in Example 9 (b) with a mixture of 50 ml of pyridine and 50 ml acetic anhydride. The crude triacetate was purified as in Example 9 (b) and then converted analogously to Example 9 (c) into the pure title compound. 4 g pure amorphous 3',4',5'-trihydroxy-3-{[4-(2-pyridyl)piperazin-1-yl]-carbonyl} flavone were obtained.

Empirical formula: $C_{25}H_{21}N_3O_6$; Molecular weight: 459.46.

(b) The title compound was reacted with hydrogen chloride gas analogously to Example 1 (c). The monohydrochloride was obtained. Empirical formula:

$C_{25}H_{22}N_3O_6Cl.0.7H_2O$; Molecular weight: 508.79; Melting point 244°-250° C.

Example 11

3',4',5'-Tripivaloyloxy-3-{[4-(2-pyridyl)-piperazin-1-yl]-carbonyl} flavone 4.0 g of 3',4',5'-trihydroxy-3-{[4-(2-pyridyl)-piperazin-1-yl]-carbonyl)} flavone were dissolved in 50 ml absolute pyridine, and the solution was reacted with 3.2 ml pivaloyl chloride. The reaction mixture was allowed to stand at room temperature for twelve hours. Then for working up, it was poured onto 150 ml of an ice/water mixture and extracted with methylene chloride. The methylene chloride phase was separated, dried over sodium sulfate, concentrated and treated three more times with toluene and again concentrated. The remaining residue was purified by column chromatography on silica gel under slightly elevated pressure using ethyl acetate/dichloromethane 8:2 as the eluent. 2.3 g crystalline 3',4',5'-tripivaloyloxy-3-{[4-(2-pyridyl)-piperazin-1-yl]-carbonyl} flavone were obtained which crystallized with ½ mol water. Empirical formula $C_{40}H_{45}N_3O_9$; Molecular weight 720.82; Melting point: 120°-125° C.

EXAMPLE 12

3', 4',5'-Trimethoxy-3-{2-[4-(2-pyridyl)-piperazin-1-yl]-ethylaminocarbonyl} flavone (a) For conversion into a mixed anhydride, 7.13 g 3',4',5'-trimethoxyflavone-3-carboxylic acid were dissolved in 100 ml absolute dichloromethane, cooled to −20° C. and reacted with 4.9 g dimethylaminopyridine and 1.9 ml mesylchloride under exclusion of moisture. The reaction mixture was allowed to react for ten minutes at −20° C.

(b) 1.33 ml 2-aminoethanol were added to the reaction solution produced above containing the mixed anhydride of 3',4',5'-trimethoxyflavone-3-carboxylic acid. The reaction mixture was allowed to warm up to room temperature and was stirred for a time. The mixture was then worked up by adding it to saturated sodium bicarbonate solution, separating the organic phase and extracting the aqueous phase once more with dichloromethane. The combined dichloromethane phases were dried over sodium sulfate and concentrated. The 3',4',5'-trimethoxy-3-(2hydroxyethylaminocarbonyl) flavone which partially crystallized was separated. After further concentration, another part of the product crystallized from the mother liquor. In total 6.2 g were obtained.

(c) 0.4 g of 3',4',5'-trimethoxy-3-(2-hydroxyethylaminocarbonyl) flavone were dissolved in 20 ml dichloromethane. The solution was reacted with 0.2 ml phosphorus tribromide, briefly warmed to 60° C. and then allowed to stand twelve more hours at room temperature. The reaction mixture was worked up by pouring onto ice water, separating the organic phase, washing three times with saturated sodium bicarbonate solution, drying over sodium sulfate and concentrating. The remaining residue was taken up in ether. 0.3 g of 3',4',5'-trimethoxy-3-(2-bromoethylaminocarbonyl) flavone crystallized from ether solution. This was further processed directly.

(d) 0.2 g of 3',4',5'-trimethoxy-3-(2-bromoethylamino-carbonyl) flavone were dissolved in 10 ml dichloromethane, and the solution was reacted with a spatula tip full of potassium iodide and 0.5 ml 1-(2-pyridyl)-piperazine. The reaction mixture was heated at reflux temperature for one hour. After cooling, the reaction mixture was worked up by adding further dichloromethane and shaking with saturated sodium carbonate solution and water. Then the organic phase was dried over sodium sulfate, concentrated, and the residue was purified by column chromatography on silica gel under slightly elevated pressure (flash chromatography) using tetrahydrofuran/ethylacetate 1:1 as the eluent. In this way 3',4',5'-trimethoxy-3-{2-[4-(2-pyridyl)-piperazin-1-yl]-ethylamino-carbonyl) flavone was obtained in pure amorphous form.

Empirical formula: $C_{30}H_{32}N_4O_6$; Molecular weight 546.36.

(e) The title compound was reacted with hydrogen chloride gas analogously to Example 1 (c). The amorphous hydrochloride of the title compound was obtained.

Empirical formula: $C_{30}H_{32}N_4O_6.2.7HCl.3.9H_2O$; Molecular weight 713.32.

EXAMPLE 13

3',4',5'-Trimethoxy-3-(piperazin-1-yl-carbonyl) flavone 0.4 g of 3',4',5'-Trimethoxy-3-[(4-benzylpiperazin-1 yl)-carbonyl] flavone were dissolved in 10 ml ethanol. To the solution were added 1 ml concentrated hydrochloric acid and palladium/carbon (5%) as catalyst. Hydrogenation was then carried out at a hydrogen pressure of 5 bars for five hours. Subsequently the catalyst was filtered out and the filtrate was concentrated. 210 mg of the hydrochloride of the amorphous title compound were obtained.

Empirical formula: $C_{23}H_{24}N_2O_6.1HCl$; Molecular weight: 460.70.

EXAMPLE 14

3',4',5'-Trihydroxy-3-[(4-benzylpiperazin-1-yl-carbonyl] flavone (a) 4.0 g of 3',4',5'-trimethoxyflavone-3-carboxylic acid were added to 200 ml of absolute dichloromethane and reacted with 82 ml of a 1 molar boron tribromide solution in absolute dichloromethane under a nitrogen atmosphere at 0° C. The reaction mixture was stirred for twelve hours during which it was allowed to warm to room temperature. Then, for working up, water was carefully added under ice cooling, then made up to twice the volume with water and intensively stirred. The resulting 3',4',5'-trihydroxyflavone-3-carboxylic acid precipitated and was filtered out. The filter cake was washed with water several times and recrystallized from methanol. 3 g of pure 3',4',5'-trihydroxyflavone-3-carboxylic acid were obtained.

Empirical formula: $C_{16}H_{10}O_7.1H_2O$; Molecular weight: 332.27; Melting point 230° C.

(b) 3',4',5'-Trihydroxyflavone-3-carboxylic acid was dissolved in 4 ml absolute pyridine, and the solution was reacted with 0.57 ml acetic anhydride and stirred for two hours. Then it was worked up by diluting with 20 ml dichloromethane, pouring onto a mixture of dilute hydrochloric acid/ice water and shaking with dichloromethane. Here care must be taken that the aqueous phase remains acid (if necessary some dilute hydrochloric acid must be added). The dichloromethane phase was separated, washed with water, dried over sodium sulfate and evaporated. 0.8 g crude 3',4',5'-triacetoxyflavone-3-carboxylic acid were obtained which was immediately processed further without additional purification.

(c) The crude 3',4',5'-triacetoxyflavone-3-carboxylic acid obtained above was dissolved in 10 ml dichloromethane and was reacted with 0.44 g dimethylaminopyridine and 0.16 ml mesylchloride under exclusion of moisture at −20° C. to convert it into the mixed anhydride. The reaction mixture was allowed to react until no more free acid could be detected by thin layer chromatography.

(d) An excess of 4-benzylpiperazine (1 ml) was added to the reaction solution prepared above containing the mixed anhydride. In order to form the title compound, the reaction mixture was stirred for a further ten minutes at −20° C. and for one hour at room temperature. Then the reaction mixture was concentrated for working up, the remaining residue taken up in methanol, the methanolic solution allowed to stand a while to assure complete deacylation, then concentrated, the residue taken up in water and extracted with ethyl acetate. The organic phase was separated, dried over sodium sulfate and concentrated. The residual crude title compound was purified by column chromatography on silica gel under slightly elevated pressure (flash chromatography) using dichloromethane/methanol 1:1 as the eluent. 200 mg of 3',4',5'-trihydroxy-3-[(4benzylpiperazin-1-yl)-carbonyl] flavone were obtained.

Empirical formula: $C_{27}H_{24}N_2O_6 \cdot 1.2H_2O$; Molecular weight: 494.12; Melting point: 168°–170° C.

(e) The title compound was converted into its monotartrate analogously to Example 2 (b), whereupon the 3',4',5'-trihydroxy-3[(4-benzylpiperazin-1-yl)-carbonyl] flavone tartrate dihydrate crystallized out.

Empirical formula: $C_{31}H_{30}N_2O_{12} \cdot 2H_2O$; Molecular weight: 658.60; Melting point 160°–165° C.

In accordance with the processes described in the foregoing examples it is also possible to produce the compounds of Formula I listed in the following Table 1.

In accordance with the processes described in Example 6 (a)–6 (d) it is possible to prepare the specific flavone-3-carboxylic acids of Formula II and their salts listed in the following Table 2.

TABLE 1

| Example No. | $R^1$ | $R^2$ | $R^3$ | $R^4$ | $R^5$ | $R^6$—Z— | Comments<br>E = Empirical Formula<br>MW = Molecular Weight<br>MP = Melting Point in °C. |
|---|---|---|---|---|---|---|---|
| 15 | 4'-O—(CH$_2$)$_{19}$—CH$_3$ | H | H | H | H | 4-(2-pyrid)-pip- | HCl: E = $C_{45}H_{61}N_3O_4 \cdot 2HCl$<br>MW = 780.92 am |
| 16 | H | | H | H | H | 4-CH$_3$—pip- | (a) B: E = $C_{21}H_{20}N_2O_3$<br>MW = 348.4<br>MP: 187–190<br>(b) Tart.0.25H$_2$O<br>E = $C_{25}H_{26}N_2O_9 \cdot 0.25H_2O$<br>MW = 503<br>MP: 203–205 |
| 17 | H | | H | H | H | 4-(2-pyrim)-pip- | B: E = $C_{24}H_{20}N_4O_3$<br>MW = 412.44<br>MP: 191 |
| 18 | H | | H | H | H | 1-benz-pipe-NH— | (a) B: E = $C_{28}H_{26}N_2O_3$<br>MW = 438.52<br>MP: 183–185<br>(b) Tart.1.1H$_2$O<br>E = $C_{32}H_{32}N_2O_9 \cdot 1.1H_2O$<br>MW = 608.43<br>MP: 123–126 |
| 19 | H | | H | H | H | (C$_2$H$_5$)$_2$N—(CH$_2$)$_3$—NH— | B: E = $C_{23}H_{26}N_2O_3 \cdot 0.3H_2O$<br>MW = 383.88<br>MP: 143–145 |
| 20 | H | | H | H | H | pyrro-(CH$_2$)$_2$—NH— | (a) B: E = $C_{22}H_{22}N_2O_3 \cdot 0.1H_2O$<br>MW = 364.23<br>MP: 137–138<br>(b) HCl: E = $C_{22}H_{23}N_2O_3Cl \cdot 2.2H_2O$<br>MW = 438.52 am |
| 21 | H | | H | H | H | morph-(CH$_2$)$_3$—NH— | (a) B: E = $C_{23}H_{24}N_2O_4$<br>MW = 392.42<br>MP: 147–149<br>(b) HCl: E = $C_{23}H_{25}N_2O_4Cl \cdot 1.6H_2O$<br>MW = 457.75 am |
| 22 | H | | H | H | H | (C$_2$H$_5$)$_2$N—(CH$_2$)$_2$—NH— | (a) B: E = $C_{22}H_{24}N_2O_3$<br>MW = 364.45<br>MP: 147–148<br>(b) HCl: E = $C_{22}H_{24}N_2O_3 \cdot 0.2H_2O$<br>MW = 402.69 am |
| 23 | H | | H | H | H | 4-benz-pip-(CH$_2$)$_4$—NH— | HCl: E = $C_{31}H_{33}N_3O_3 \cdot 2.35HCl \cdot 3.3H_2O$<br>MW = 640.98 am |
| 24 | H | | H | H | H | 4-CH$_3$—pip-(CH$_2$)$_4$—NH— | B: E = $C_{25}H_{30}N_3O_3$<br>MW = 419.53;<br>MP: 133–134 |
| 25 | H | | H | H | H | 4-(2-pyrim)-pip-(CH$_2$)$_4$—NH— | HCl: E = $C_{28}H_{29}N_5O_3 \cdot 2.5HCl \cdot 3.66H_2O$<br>MW = 640.66;<br>MP: 139–148 |
| 26 | H | | H | H | H | 4-(2-pyrid)-pip-(CH$_2$)$_4$—NH— | N,N,N-Trioxid:<br>E = $C_{29}H_{30}N_4O_6 \cdot 3.8H_2O$<br>MW = 599.05;<br>MP: 125(Z) |
| 27 | H | | H | H | H | 4-(4-F-phen)-pip-(CH$_2$)$_4$—NH— | HCl: E = $C_{30}H_{30}N_3O_3F \cdot 2HCl \cdot 1.5H_2O$<br>MW = 599.53 am |
| 28 | 4'-OCH$_3$ | | H | H | H | 4-CH$_3$—pip- | Tart: E = $C_{26}H_{28}N_2O_{10} \cdot 1H_2O$ |

TABLE 1-continued

| Example No. | R¹ | R² | R³ | R⁴ | R⁵ | R⁶—Z— | Comments<br>E = Empirical Formula<br>MW = Molecular Weight<br>MP = Melting Point in °C. |
|---|---|---|---|---|---|---|---|
| 29 | 3'-OH | 4'-OH | H | H | H | 4-(2-pyrid)-pip- | MW = 546.53;<br>MP: 202-209<br>B: E = $C_{25}H_{21}N_3O_5$<br>MW = 443.46<br>MP: 243 |
| 30 | 3'-OH | H | H | H | H | 4-benz-pip- | Tart: E = $C_{31}H_{30}N_2O_{10}.2H_2O$<br>MW = 626.62 am |
| 31 | 3'-OCH₃ | H | H | H | H | 4-benz-pip- | HCl: E = $C_{28}H_{27}N_2O_4Cl.1.7H_2O$<br>MW = 521.62 am |
| 32 | 3',4'-di-OCH₃ | | H | H | H | 4-(2-pyrid)-pip- | (a) B: E = $C_{27}H_{25}N_3O_5.0.4H_2O$<br>MW = 478.72<br>MP: 94-97<br>(b) HCl: E = $C_{27}H_{26}N_3O_5Cl.2.3H_2O$<br>MW = 549.4<br>MP: 141-145 |
| 33 | 3',4'-di-OCH₃ | | H | H | H | 4-benz-pip- | HCl: E = $C_{29}H_{29}N_2O_5Cl.0.2H_2O$<br>MW = 524.61<br>MP: 149-153 |
| 34 | H | | H | H | 5,7-di-OCH₃ | 4-(2-pyrid)-pip- | HCl: E = $C_{27}H_{25}N_3O_5.1.1HCl.2H_2O$<br>MW = 547.65 am |
| 35 | 2'-Cl | | H | H | H | 4-(2-pyrid)-pip- | HCl: E = $C_{25}H_{26}N_3O_3Cl.1.3HCl.1.6H_2O$<br>MW = 522.13<br>MP: 130-140 |
| 36 | 4'-OC₁₆H₃₃ | H | H | H | H | 4-benz-pip- | B: E = $C_{43}H_{56}N_2O_4$<br>MW = 664.93<br>MP: 76-80 |
| 37 | 4'-OC₁₆H₃₃ | H | H | H | H | 4-(2-pyrid)-pip- | B: E = $C_{41}H_{53}N_3O_4$<br>MW = 651.89<br>MP: 87-90 |
| 38 | 4'-OC₁₆H₃₃ | H | H | H | H | 4-benz-pip-(CH₂)₄—NH— | B: E = $C_4$-$H_{65}N_3O_4$<br>MW = 736.06; MP: 83 |
| 39 | 3',4',5'-tri-O—CO—CH₃ | | H | H | H | 4-(2-pyrid)-pip- | (a) B: E = $C_{31}H_{27}N_3O_9.1H_2O$<br>MW = 603.59<br>MP: 115-120<br>(b) Tart: E = $C_{35}H_{33}N_3O_{15}.2H_2O$<br>MW = 771.69<br>MP: 184-188 |
| 40 | 3',4',5'-tri-OCH₃ | | | H | H | pyrro-(CH₂)₂—NH— | (a) B: E = $C_{25}H_{28}N_2O_6.0.5H_2O$<br>MW = 461.52<br>MP: 129-133<br>(b) HCl: E = $C_{25}H_{29}N_2O_6Cl.1.1H_2O$<br>MW = 508.79<br>MP: 105-110 |
| 41 | 3',4',5'-tri-OCH₃ | | | H | H | (C₂H₅)₂N—(CH₂)₃—NH— | (a) B: E = $C_{26}H_{32}N_2O_6$<br>MW = 468.55<br>MP: 120-122<br>(b) Tart: E = $C_{30}H_{38}N_2O_{12}.1H_2O$<br>MW = 636.65<br>MP: 82-86 |
| 42 | 3',4',5'-tri-O—CO—CH₃ | | | H | H | 4-benz-pip- | (a) B: E = $C_{33}H_{30}N_2O_9.0.3H_2O$<br>MW = 604.01<br>MP: 198-204<br>(b) Tart: E = $C_{37}H_{36}N_2O_{15}.2H_2O$<br>MW = 784.74<br>MP: 135-142 |
| 43 | 3',4',5'-tri-OCH₃ | | | H | H | (C₂H₅)₂N—(CH₂)2-NH— | (a) B: E = $C_{25}H_{30}N_2O_6.0.1H_2O$<br>MW = 456.32<br>MP: 117-120<br>(b) Tart: E = $C_{29}H_{36}N_2O_{12}.1H_2O$<br>MW = 622.63<br>MP: 85-89 |
| 44 | 3',4',5'-tri-OCH₃ | | | H | H | morph-(CH₂)₂—NH— | B: E = $C_{26}H_{30}N_2O_7.0.2H_2O$<br>MW = 486.13<br>MP: 106-109 |
| 45 | 3',4',5'-tri-OCH₃ | | | H | H | (C₂H₅)₂N—(CH₂)₃—O— | HCl: E = $C_{26}H_{32}NO-Cl.1.5H_2O$<br>MW = 533.02 am |
| 46 | 3',4',5'-tri-OCH₃ | | | H | H | morph-(CH₂)₃—NH— | Tart: E = $C_{30}H_{36}N_2O_{13}.1.5H_2O$<br>MW = 659.64<br>MP: 95-104 |
| 47 | 3',4',5'-tri-OCH₃ | | | H | H | 4-(2-pyrid)-pip-(CH₂)₂—O— | di-HCl: E = $C_{30}H_{35}N_3O-Cl_2.2H_2O$<br>MW = 654.54<br>MP: 160-164 |
| 48 | 3',4',5'-tri-OCH₃ | | | H | H | (2-pyrid)-(CH₂)₂—NH— | HCl: E = $C_{26}H_{25}N_2O_6Cl.1.2H_2O$<br>MW = 518.57<br>MP: 123-127 |
| 49 | 3',4',5'-tri-OCH₃ | | | H | H | pyrro-(CH₂)₂—O— | HCl: E = $C_{25}H_2$-NO-.1.1HCl.1.3H₂O<br>MW = 517.02 |

TABLE 1-continued

| Example No. | R¹ | R² | R³ | R⁴ | R⁵ | R⁶—Z— | Comments<br>E = Empirical Formula<br>MW = Molecular Weight<br>MP = Melting Point in °C. |
|---|---|---|---|---|---|---|---|
| 50 | 3',4',5'-tri-OCH₃ | | | H | H | (2-pyrid)-(CH₂)₂—O— | MP: 105-108<br>HCl: E = C₂₆H₂₄NO₇Cl.1H₂O<br>MW = 515.95 |
| 51 | 3',4',5'-tri-OCH₃ | | | H | H | 4-benz-pip-(CH₂)₄—NH— | MP: 99-103<br>di-HCl: E = C₃₄H₄₁N₃O₆Cl₂.2H₂O.0.2CH₂Cl₂<br>MW = 711.64 am |
| 52 | 3',4',5'-tri-OCH₃ | | | H | H | 4-benz-pip-(CH₂)₄—NH— | N,N-Dioxid: E = C₃₄H₃₉N₃O₈.3H₂O.3H₂O<br>MW = 671.71 am |
| 53 | 3',4',5'-tri-OH | | | H | H | (2-pyrid)-(CH₂)₂—NH— | HCl: E = C₂₃H₁₉N₂O₆Cl.1.2H₂O<br>MW = 476.48 |
| 54 | 3',4',5'-tri-OCH₃ | | | H | H | 4-(2-pyrim)-pip-(CH₂)₄—NH— | MP: 135-140<br>di-HCl: E = C₃₁H₃₅N₅O₆.2.8HCl.4.67H₂O<br>MW = 759.88 |
| 55 | 3',4',5'-tri-OCH₃ | | | H | H | 4-(2-pyrid)-pip-(CH₂)₂—NH— | MP: 130-136<br>N,N,N-Trioxid:<br>E = C₃₂H₃₆N₄O₉.2.9H₂O<br>MW = 672.91 |
| 56 | 3',4',5'-tri-O—CO—C₂H₅ | | | H | H | 4-(2-pyrid)-pip- | MP: 125(Z)<br>B: E = C₃₄H₃₃N₃O₉<br>MW = 627.65 |
| 57 | 3',4',5'-tri-O—CO—CH(CH₃)₂ | | | H | H | 4-(2-pyrid)-pip- | MP: 139-144<br>B: E = C₃₇H₃₉N₃O₉<br>MW = 669.73 |
| 58 | 3',4',5'-tri-O—CO—(CH₂)₂CH₃ | | | H | H | 4-(2-pyrid)-pip- | MP: 194-196<br>B: E = C₃₇H₃₉N₃O₉<br>MW = 669.73 |
| 59 | 3',4',5'-tri-OCH₃ | | | H | H | 4-(4-F-benz)-pip-(CH₂)₄—NH— | MP: 136-139<br>HCl: E = C₃₅H₃₆N₃O₆F.2HCl.7.7H₂O<br>MW = 801.31 am |
| 60 | 3'-Cl | H | H | 6-CH₃ | H | 4-(2-pyrid)-pip- | (a) B: E = C₂₆H₂₂N₃O₃Cl<br>MW = 459.93<br>MP: 194-197<br>(b) HCl: E = C₂₆H₂₂N₃O₃Cl.1.2HCl.1.0H₂O<br>MW = 521.70<br>MP: 142-146 |
| 61 | 4'-OCH₃ | H | H | 5,7-di-OCH₃ | | 4-(2-pyrid)-pip- | HCl: E = C₂₈H₂₇N₃O₆.2HCl<br>MW = 574.46 am |
| 62 | 4'-OH | H | H | 5,7-di-OH | | 4-(2-pyrid)-pip- | HCl: E = C₂₅H₂₁N₃O₆.2HCl<br>MW = 532.37 am |
| 63 | 3',4',5'-tri-OCH₃ | | | H | H | 4-CH₃—pip-(CH₂)₄—NH | HCl: E = C₂₈H₃₅O₆N₃.2.6HCl.3.4H₂O<br>MW = 664.13 am |
| 64 | 3',4',5'-tri-OCH₃ | | | H | H | 4-(2-C₂H₅-phen)-pip-(CH₂)₄—NH— | B: E = C₃₅H₄₁N₃O₆<br>MW = 599.73<br>MP: 176-177 |
| 65 | 3',4',5'-tri-OCH₃ | | | H | H | 4-(2-pyrid)-pip-(CH₂)₃—NH— | HCl: E = C₃₁H₃₄O₆N₄.2.1HCl.3.2H₂O<br>MW = 692.82 am |
| 66 | 3',4',5'-tri-OCH₃ | | | H | H | pip-(CH₂)₄—NH— | HCl: E = C₂₇H₃₃N₃O₆.2HCl<br>MW = 568.94 am |

B = Base
Z = under decomposition
benz = Benzyl
morph = Morpholin-1-yl
Tart = Tartrate
pip = Piperazin-1-yl
pipe = Piperidin-4-yl
HCl = Hydrochloride
pyrim = 1,3-Pyrimidyl
phen = Phenyl
am = amorphous
pyrid = Pyridyl
pyrro = Pyrrolidin-1-yl

TABLE 2

| Example No. | R¹ | R² | R³ | R⁴ | R⁵ | Comments<br>E = Empirical Formula<br>MW = Molecular Weight<br>MP = Melting Point in °C. |
|---|---|---|---|---|---|---|
| 101 | H | H | H | H | H | (a) FA: E = C₁₆H₁₀O₄<br>MW = 266.25 MP: 178-180<br>(b) Na-Salt: E = C₁₆H₉O₄Na<br>MW = 288.23 MP: 314-317 |
| 102 | 3'-OCH₃ | H | H | H | H | (a) FA: E = C₁₇H₁₂O₅<br>MW = 296.28 MP: 171-173 |

TABLE 2-continued

| Example No. | R¹ | R² | R³ | R⁴ | R⁵ | Comments<br>E = Empirical Formula<br>MW = Molecular Weight<br>MP = Melting Point in °C. |
|---|---|---|---|---|---|---|
| | | | | | | (b) Na-Salt: E = $C_{17}H_{11}O_5Na$; $0.3H_2O$<br>MW = 323.66 MP: 308-310 |
| 103 | 4'-OCH₃ | H | H | H | H | FA: E = $C_{17}H_{12}O_5$<br>MW = 296.28 MP: 187-190 |
| 104 | 3',4',5'-tri-OCH₃ | | | H | H | (a) FA: E = $C_{19}H_{16}O_7$<br>MW = 356.33 MP: 260-262 |
| | | | | | | (b) Na-Salt: E = $C_{19}H_{15}O_7Na$; $1.8H_2O$<br>MW = 410.74 MP: 206-210 |
| 105 | 3',4',5'-tri-OH | | | H | H | (a) FA: E = $C_{16}H_{10}O_7$; $1H_2O$<br>MW = 332.27 am |
| | | | | | | (b) Na-Salt: E = $C_{16}H_9O_7Na$; $1.1H_2O$<br>MW = 356.05 am |
| 106 | 3',4'-di-OH | | H | H | H | FA: E = $C_{16}H_{10}O_6$<br>MW = 298.25 MP: 248-252 |
| 107 | 3'-Cl | H | H | 6-CH₃ | H | FA: E = $C_{17}H_{11}O_4Cl$<br>MW = 314.73 MP: 217-219 |
| 108 | 2'-Cl | H | H | H | H | FA: E = $C_{16}H_9O_4Cl$<br>MW = 300.70 MP: 140-143 |
| 109 | 4'-OCH₃ | H | H | 5,7-di-OCH₃ | | FA: E = $C_{19}H_{16}O_7$<br>MW = 356.35 MP: 234-238 |
| 110 | H | H | H | 5,7-di-OCH₃ | | FA: E = $C_{18}H_{14}O_6$<br>MW = 326.32 MP: 227-229 |
| 111 | 4'-OH | H | H | 5,7-di-OH | | FA: E = $C_{16}H_{10}O_7$<br>MW = 314.26 MP: 278-285 |
| 112 | 3',4'-di-OCH₃ | | H | H | | FA: E = $C_{18}H_{14}O_6$<br>MW = 326.31 am |
| 113 | 4'-O—(CH₂)₁₅—CH₃ | H | H | H | H | FA: E = $C_{32}H_{42}O_5$<br>MW = 505.68 MP: 132-135 |
| 114 | 4'-OCH₃ | H | H | 7-OCH₃ | H | FA: E = $C_{18}H_{14}O_6$<br>MW = 326.31 MP: 239-245 |
| 115 | 4'-OC₂₀H₄₁ | H | H | H | H | FA: E = $C_{36}H_{50}O_5$<br>MW = 562.79 MP: 130-134 |

FA = free acid
Na-Salt = sodium salt

EXAMPLE I

Tablets containing
3-{[4-(2-Pyridyl)-piperazin-1-yl]-carbonyl} flavone hydrochloride Tablets having the following composition per tablet were produced:

| | |
|---|---|
| 3-{[4-(2-pyridyl)-piperazin-1-yl]-carbonyl} flavone hydrochloride | 20 mg |
| Cornstarch | 60 mg |
| Lactose | 135 mg |
| Gelatine (as 10% solution) | 6 mg |

The active compound, the cornstarch and the lactose were bodied with the 10% gelatine solution. The paste was comminuted, and the resulting granulate was placed on a suitable plate and dried. The dried granulate was passed through a pulverizer and was mixed in a mixer with the following additional adjuvants:

| | |
|---|---|
| Talc | 5 mg |
| Magnesium stearate | 5 mg |
| Cornstarch | 9 mg |
| and pressed into 240 mg tablets. | |

The foregoing description and examples have been set forth merely to illustrate the invention and are not intended to be limiting. Since modifications of the described embodiments incorporating the spirit and substance of the invention may occur to persons skilled in the art, the scope of the invention should be construed in accordance with the appended claims and equivalents.

We claim:

1. A 3-flavone carboxylic acid compound corresponding to the Formula II

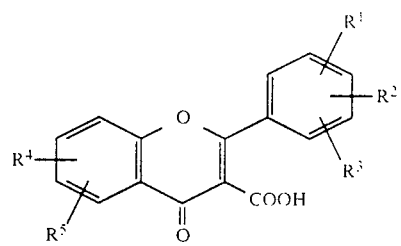

wherein R¹, R² and R³ are in the 3'-, 4'- and 5'-positions, and

R¹ represents hydrogen, lower alkyl, halogen hydroxy, lower alkylcarbonyloxy or an R⁹-O group, wherein R⁹ represents an alkyl or alkenyl group with up to 20 carbon atoms, R² represents hydrogen, lower alkyl, halogen, hydroxy, lower alkylcarbonyloxy or an R⁹-O group, wherein R⁹ has the above meaning, and R³ represents hydrogen, lower alkyl, halogen, hydroxy, lower alkylcarbonyloxy or an R⁹-O group, wherein R⁹ has the above meaning, or two of the substituent groups R¹ to R³ are bonded to adjacent carbon atoms and together represent an alkylene dioxy group with 1-2 carbon atoms, with the proviso that if more than one of the substituent groups $R^1$ to $R^3$ represent oxygen-containing groups, these groups are identical, $R^4$ represents hydrogen, lower alkyl, halogen, hydroxy, lower alkylcarbonyloxy or an $R^9$-O group, wherein $R^9$ has the above meaning, and $R^5$ represents hydrogen, lower alkyl, halogen, hydroxy, lower alkylcarbonyloxy or an $R^9$-O group, wherein $R^9$ has the above meaning, or $R^4$ and $R^5$ are bonded to adjacent carbon atoms and together form an alkylene chain with 1 or 2 carbon atoms, wherein if $R^4$ and $R^5$ represent oxygen-containing groups, these groups are identical, and, if $R^1$, $R^2$ or $R^3$ represents hydroxy, oxygen-containing groups $R^4$ or $R^5$ also represent hydroxy, and at least one of the substituents $R^1$ to $R^5$ being other than hydrogen, and if $R^1$, $R^2$ and $R^3$ represent hydrogen and $R^4$ represents 5-methyl, $R^5$ is other than 7-methyl, or a salt thereof.

* * * * *